United States Patent
Zhang et al.

(10) Patent No.: US 8,503,763 B2
(45) Date of Patent: Aug. 6, 2013

(54) IMAGE SIGNATURES FOR USE IN MOTION-BASED THREE-DIMENSIONAL RECONSTRUCTION

(75) Inventors: Tong Zhang, Wellesley, MA (US); Ramakrishna Raghavan, Chennai (IN); Janos Rohaly, Acton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 344 days.

(21) Appl. No.: 12/811,242

(22) PCT Filed: Jan. 4, 2009

(86) PCT No.: PCT/US2009/030066
§ 371 (c)(1),
(2), (4) Date: Nov. 15, 2010

(87) PCT Pub. No.: WO2009/089127
PCT Pub. Date: Jul. 16, 2009

(65) Prior Publication Data
US 2011/0164810 A1    Jul. 7, 2011

Related U.S. Application Data

(60) Provisional application No. 61/019,159, filed on Jan. 4, 2008.

(51) Int. Cl.
*G06K 9/00* (2006.01)
(52) U.S. Cl.
USPC .......................................... 382/154
(58) Field of Classification Search
None
See application file for complete search history.

(56) References Cited

U.S. PATENT DOCUMENTS

| | | | |
|---|---|---|---|
| 6,219,437 B1 | 4/2001 | Baldur | |
| 6,973,204 B2 | 12/2005 | Adachi | |
| 7,085,323 B2 | 8/2006 | Hong | |
| 7,372,642 B2 | 5/2008 | Rohaly et al. | |
| 7,508,430 B1 * | 3/2009 | Oten et al. | 348/242 |

(Continued)

FOREIGN PATENT DOCUMENTS

KR    2007-0039641    4/2007

OTHER PUBLICATIONS

Dorst, "First Order Propagation of the Procrustes Method for 3D Attitude Estimation", IEEE Transactions on Pattern Analysis and Machine Intelligence, vol. 27, No. 2, Feb. 2005, pp. 221-229.

(Continued)

*Primary Examiner* — Nirav G Patel

(57) ABSTRACT

A family of one-dimensional image signatures is obtained to represent each one of a sequence of images in a number of translational and rotational orientations. By calculating these image signatures as images are captured, a new current view can be quickly compared to historical views in a manner that is less dependent on the relative orientation of a target and search image. These and other techniques may be employed in a three-dimensional reconstruction process to generate a list of candidate images from among which full three-dimensional registration may be performed to test for an adequate three-dimensional match. In another aspect this approach may be supplemented with a Fourier-based approach that is selectively applied to a subset of the historical images. By alternating between spatial signatures for one set of historical views and spatial frequency signatures for another set of historical views, a pattern matching system may be implemented that more rapidly reattaches to a three-dimensional model in a variety of practical applications.

20 Claims, 10 Drawing Sheets

U.S. PATENT DOCUMENTS

| | | |
|---|---|---|
| 7,605,817 B2 | 10/2009 | Zhang et al. |
| 2001/0016063 A1 | 8/2001 | Albeck et al. |
| 2001/0033326 A1 | 10/2001 | Goldstein et al. |
| 2002/0136444 A1 | 9/2002 | Brown et al. |
| 2004/0051783 A1 | 3/2004 | Chellappa et al. |
| 2004/0197728 A1 | 10/2004 | Abolfathi et al. |
| 2005/0089213 A1 | 4/2005 | Geng |
| 2005/0089214 A1 | 4/2005 | Rubbert et al. |
| 2005/0089822 A1 | 4/2005 | Geng |
| 2005/0285874 A1 | 12/2005 | Zitnick, II et al. |
| 2006/0154198 A1 | 7/2006 | Durbin et al. |
| 2006/0204076 A1 | 9/2006 | Avinash et al. |
| 2007/0031064 A1 | 2/2007 | Zhao et al. |
| 2007/0103460 A1 | 5/2007 | Zhang et al. |
| 2007/0127813 A1 | 6/2007 | Shah |
| 2007/0141534 A1 | 6/2007 | Wen |
| 2007/0172101 A1 | 7/2007 | Kriveshko et al. |
| 2007/0172112 A1 | 7/2007 | Paley et al. |
| 2007/0253618 A1 | 11/2007 | Kim et al. |

OTHER PUBLICATIONS

Zhang, "Hierarchical Block-Based Disparity Estimation Using Mean Absolute Difference and Dynamic Programming", Proc. Of the Int. Workshop on Very Low Bitrate Video Coding, pp. 114, 118, Athens Greece, Oct. 11-12, 2001.

Kriveshko et al., U.S. Appl. No. 12/811,268, filed Jun. 30, 2010.

Rohaly et al., U.S. Appl. No. 12/811,236, filed Sep. 22, 2010.

Rohaly et al., U.S. Appl. No. 12/811,237, filed Sep. 27, 2010.

Zhang et al., U.S. Appl. No. 12/811,239, filed Sep. 22, 2010.

Triggs et al., "Bundle adjustment—a modern synthesis" Vision algorithms: theory and practice (2000) pp. 153-177.

* cited by examiner

IMAGE SIGNATURES FOR USE IN MOTION-BASED THREE-DIMENSIONAL RECONSTRUCTION

CROSS REFERENCE TO RELATED APPLICATIONS

This application is a national stage filing under 35 U.S.C. 371 of PCT/US2009/030066, filed Jan. 4, 2009, which claims priority to U.S. Provisional Application No. 61/019,159, filed Jan. 4, 2008, the disclosure of which is incorporated by reference in their entirety herein.

FIELD OF INVENTION

This invention relates generally to three-dimensional imaging and more specifically to image signatures to improve matching in motion-based three-dimensional reconstruction.

BACKGROUND

In one technique for three-dimensional image reconstruction, a number of images or image sets of an object are captured with a camera that travels in a path over the surface of the object. When the camera path becomes broken, either due to intentional interruption by a user or due to an inability to couple new, incoming data to an existing three-dimensional model, it may be desired to continue scanning for a reconstruction by reattaching to the existing camera path. While generic three-dimensional registration is conceptually possible in order to relate a current view from a camera to one or more existing frames of image data in an existing camera path used for a reconstruction, this approach becomes impractical when the three-dimensional model is formed from hundreds or thousands of frames of image data including millions of surfaces or three-dimensional points.

There remains a need for improved techniques for finding a good match for a current camera view from among many existing frames of image data.

SUMMARY

A family of one-dimensional image signatures is obtained to represent each one of a sequence of images in a number of translational and rotational orientations. By calculating these image signatures as images are captured, a new current view can be quickly compared to historical views in a manner that is less dependent on the relative orientation of a target and search image. These and other techniques may be employed in a three-dimensional reconstruction process to generate a list of candidate images from among which full three-dimensional registration may be performed to test for an adequate three-dimensional match. In another aspect this approach may be supplemented with a Fourier-based approach that is selectively applied to a subset of the historical images. By alternating between spatial signatures for one set of historical views and spatial frequency signatures for another set of historical views, a pattern matching system may be implemented that more rapidly reattaches to a three-dimensional model in a variety of practical applications.

In one aspect, a method for creating a signature for image matching disclosed herein includes providing an image containing a plurality of pixels; creating an average for each one of a plurality of rows of pixels in a center region of the image to provide a linear array of row averages stored as a first signature; rotating the center region relative to the image to provide a rotated center image; creating an average for each one of a plurality of rows of pixels in the rotated center image to provide a linear array of rotated row averages stored as a second signature; translating the center region relative to the image to provide a translated center image; creating an average for each one of a plurality of rows of pixels in the translated center image to provide a linear array of translated row averages stored as a third signature; and determining an element-by-element row average for each signature of the image including at least the first signature, the second signature, and the third signature, and storing the element-by-element row average as a summary image signature descriptive of the image.

The image may be a compressed version of a source image having a greater number of pixels. The method may include translating the center region into a plurality of offset positions relative to the image and obtaining another linear array of row averages from the center region for each one of the plurality of offset positions. The method may include rotating the center region into a plurality of offset orientations relative to the image obtaining another linear array of row averages from the center region for each one of the plurality of offset orientations. The method may include receiving a second image; creating an average for each one of a plurality of rows of pixels in a center region of the second image to provide a linear array of row averages stored as a search signature; and comparing the summary image signature to the search signature to identify a potential match.

In another aspect a computer program product for creating a signature for image matching disclosed herein includes computer executable code embodied in a computer-readable medium that, when executing on one or more computing devices, performs the steps of providing an image containing a plurality of pixels; creating an average for each one of a plurality of rows of pixels in a center region of the image to provide a linear array of row averages stored as a first signature; rotating the center region relative to the image to provide a rotated center image; creating an average for each one of a plurality of rows of pixels in the rotated center image to provide a linear array of rotated row averages stored as a second signature; translating the center region relative to the image to provide a translated center image; creating an average for each one of a plurality of rows of pixels in the translated center image to provide a linear array of translated row averages stored as a third signature; and determining an element-by-element row average for each signature of the image including at least the first signature, the second signature, and the third signature, and storing the element-by-element row average as a summary image signature descriptive of the image.

In another aspect, a method disclosed herein for using image signatures for image matching in a three-dimensional reconstruction process includes creating an image signature for each of a plurality of images used in a three-dimensional reconstruction, each image signature including a first signature and a plurality of orientation signatures, each one of the orientation signatures calculated in the same manner as the first signature with the image in at least one of an offset rotation and an offset translation, and each image signature including a summary signature calculated as an average of the first signature and each of the orientation signatures; determining a second signature for a search image to be added to the three-dimensional reconstruction, the second signature calculated in the same manner as the first signature; selecting a number of candidate images from the plurality of images based upon a comparison of the second signature of the search image to the summary signature of each one of the plurality of images; selecting a number of candidate registrations from the candidate images based upon a comparison of the second signature to the image signature and the plurality of orientation signatures for each one of the candidate images; sequentially test registering a three-dimensional data set associated with the search image to a three-dimensional data set associated with each one of the candidate images until a resulting registration has a residual error below a predetermined threshold; and adding the search image to the plurality of images, including adding the three-dimensional data set associated with the search image to the three-dimensional reconstruction.

Each image signature may include a spatial-frequency domain representation of the image, and the second image signature may include a spatial-frequency domain representation of the search image. Each image signature may be based upon a downsampled one of the plurality of images. Each image signature may be based upon a center region of one of the plurality of images. Each one of the plurality of images may be a key frame in a camera path used to obtain the three-dimensional reconstruction. The method may include rejecting the search image when none of the resulting registrations have a residual error below the predetermined threshold; and acquiring a new search image. The method may include scaling the search image such that the three-dimensional data set associated with the search image and the three-dimensional data set associated with at least one of the plurality of images have a substantially similar centroid distance.

In another aspect, a computer program product for using image signatures for image matching in a three-dimensional reconstruction process described herein includes computer executable code embodied on a computer-readable medium that, when executing on one or more computing devices, performs the steps of: creating an image signature for each of a plurality of images used in a three-dimensional reconstruction, each image signature including a first signature and a plurality of orientation signatures, each one of the orientation signatures calculated in the same manner as the first signature with the image in at least one of an offset rotation and an offset translation, and each image signature including a summary signature calculated as an average of the first signature and each of the orientation signatures; determining a second signature for a search image to be added to the three-dimensional reconstruction, the second signature calculated in the same manner as the first signature; selecting a number of candidate images from the plurality of images based upon a comparison of the second signature of the search image to the summary signature of each one of the plurality of images; selecting a number of candidate registrations from the candidate images based upon a comparison of the second signature to the image signature and the plurality of orientation signatures for each one of the candidate images; sequentially test registering a three-dimensional data set associated with the search image to a three-dimensional data set associated with each one of the candidate images until a resulting registration has a residual error below a predetermined threshold; and adding the search image to the plurality of images, including adding the three-dimensional data set associated with the search image to the three-dimensional reconstruction.

In another aspect, a method disclosed herein for using image signatures for image matching includes creating at least one spatial signature or at least one spatial frequency signature for each one of a plurality of images; testing a first search image for a match with a first subset of the plurality of images based on a spatial signature for the first search image; and testing a second search image for a match with a second subset of the plurality of images based on a spatial frequency signature for the second search image.

The first subset may be unique from the second subset. Testing the second search image may include sequentially testing the second search image if testing the first search image fails to produce an adequate match. The plurality of images may include images used in a motion-based three-dimensional reconstruction. The first subset may include a plurality of key frames used to define a camera path in a motion-based three-dimensional reconstruction. The first subset may include all key frames for a three-dimensional scan. A plurality of spatial signatures may be calculated for each key frame that represent the key frame in a number of rotational and translational offsets. The second subset may include one or more immediately preceding images in a sequence of images obtained during a motion-based three-dimensional reconstruction. The first search image and the second search image may be sequential current views obtained from a three-dimensional camera. The method may include testing the second search image for a match with the second subset of the plurality of images based on a spatial signature for the second search image. The method may include alternately repeating a test based on a spatial signature and a test based on a spatial frequency signature for each new current view obtained from a three-dimensional camera until a match may be found according to a predetermined criterion. The method may include using the match to register a three-dimensional reconstruction for a current view to a three-dimensional model obtained from three-dimensional data associated with each of the plurality of images. The method may include discarding each new current view until the match may be found.

In another aspect, a computer program product for using image signatures for image matching disclosed herein includes computer executable code embodied on a computer-readable medium that, when executing on one or more computing devices, performs the steps of: creating at least one spatial signature or at least one spatial frequency signature for each one of a plurality of images; testing a first search image for a match with a first subset of the plurality of images based on a spatial signature for the first search image; and testing a second search image for a match with a second subset of the plurality of images based on a spatial frequency signature for the second search image.

BRIEF DESCRIPTION OF THE DRAWINGS

The invention and the following detailed description of certain embodiments thereof may be understood by reference to the following figures.

DETAILED DESCRIPTION

Figure 1:
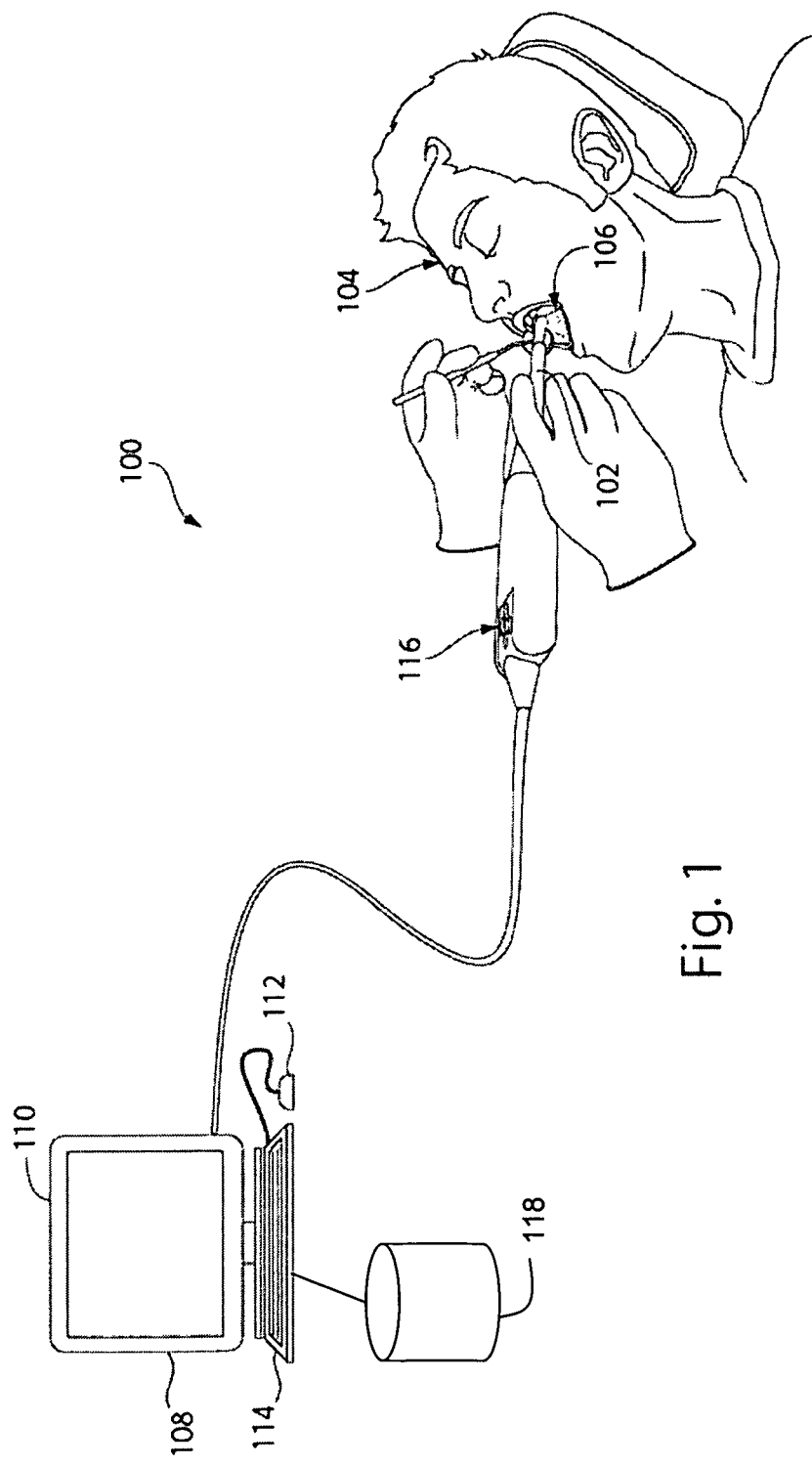
FIG. 1 shows a three-dimensional scanning system.

In the following text, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

The following description details specific scanning technologies and focuses on dental applications of three-dimensional imaging; however, it will be appreciated that the methods and systems described herein may more generally be usefully applied in any environment where a search image might be located in a number of different target images, particularly where the search image has an unknown three-dimensional position and orientation relative to the target image(s). All such variations, adaptations, and combinations apparent to one of ordinary skill in the art are intended to fall within the scope of this disclosure.

In the following description, the term "image" generally refers to a two-dimensional set of pixels forming a two-dimensional view of a subject within an image plane. The term "image set" generally refers to a set of related two-dimensional images that might be resolved into three-dimensional data. The term "point cloud" generally refers to a three-dimensional set of points forming a three-dimensional view of the subject reconstructed from a number of two-dimensional images. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional model", "three-dimensional surface representation", "digital surface representation", "three-dimensional surface map", and the like, as used herein, are intended to refer to any three-dimensional reconstruction of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that a variety of three-dimensional rendering technologies exist, and may be usefully employed with the systems and methods disclosed herein. For example, the systems and methods described herein may usefully employ a holographic display, an autostereoscopic display, an anaglyph display, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter related to dentistry. This may include intraoral structures such as dentition, and more typically human dentition, such as individual teeth, quadrants, full arches, pairs of arches (which may be separate or in occlusion of various types), soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. A tool or control may also include any physical hardware relating to the user input, such as a mouse, a keyboard, a display, a keypad, a track ball, and/or any other device that receives physical input from a user and converts the physical input into an input for use in a computerized system. Thus in the following description the terms "tool", "control" and the like should be broadly construed unless a more specific meaning is otherwise provided or clear from the context.

FIG. 1 depicts a three-dimensional scanning system that may be used with the systems and methods described herein. In general, the system 100 may include a camera 102 that captures images from a surface 106 of an object 104, such as a dental patient, and forwards the images to a computer 108, which may include a display 110 and one or more user-input devices 112, 114 such as a mouse 112 or a keyboard 114. The camera 102 may also include an integrated input or output device 116 such as a control input (e.g., button, touchpad, thumbwheel, etc.) or a display (e.g., LCD or LED display) to provide status information.

The camera 102 may include any camera or camera system suitable for capturing images from which a three-dimensional point cloud or other three-dimensional data may be recovered. For example, the camera 102 may employ a multi-aperture system as disclosed in U.S. Pat. No. 7,372,642 to Rohály et al., the entire content of which is incorporated herein by reference. While Rohály discloses one multi-aperture system, it will be appreciated that any multi-aperture system suitable for reconstructing a three-dimensional point cloud from a number of two-dimensional images may similarly be employed. In one multi-aperture embodiment, the camera 102 may include a plurality of apertures including a center aperture positioned along a center optical axis of a lens that provides a center channel for the camera 102, along with any associated imaging hardware. In such embodiments, the center channel may provide a conventional video image of the scanned subject matter, while a number of axially offset channels yield image sets containing disparity information that can be employed in three-dimensional reconstruction of a surface. In other embodiments, a separate video camera and/or channel may be provided to achieve the same result, i.e., a video of an object corresponding temporally to a three-dimensional scan of the object, preferably from the same perspective, or from a perspective having a fixed, known relationship to the perspective of the camera 102. The camera 102 may also, or instead, include a stereoscopic, triscopic or other multi-camera or other configuration in which a number of cameras or optical paths are maintained in fixed relation to one another to obtain two-dimensional images of an object from a number of different perspectives. The camera 102 may include suitable processing for deriving a three-dimensional point cloud from an image set or a number of image sets, or each two-dimensional image set may be transmitted to an external processor such as contained in the computer 108 described below. In other embodiments, the camera 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data contemporaneously with, or otherwise synchronized with, the acquisition of three-dimensional data.

In one embodiment, the camera 102 is a handheld, freely-positionable probe having at least one user-input device 116, such as a button, a lever, a dial, a thumbwheel, a switch, or the like, for user control of the image capture system 100 such as starting and stopping scans. In an embodiment, the camera 102 may be shaped and sized for dental scanning. More particularly, the camera 102 may be shaped and sized for intraoral scanning and data capture, such as by insertion into a mouth of an imaging subject and passing over an intraoral surface 106 at a suitable distance to acquire surface data from teeth, gums, and so forth. The camera 102 may, through such a continuous data acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthesis, to ensure proper fitting using a previous scan of corresponding dentition, such as a tooth surface prepared for the prosthesis.

Although not shown in FIG. 1, it will be appreciated that a number of supplemental lighting systems may be usefully employed during image capture. For example, environmental illumination may be enhanced with one or more spotlights illuminating the object 104 to speed image acquisition and improve depth of field (or spatial resolution depth). The camera 102 may also, or instead, include a strobe, a flash, or some other light source to supplement illumination of the object 104 during image acquisition.

The object 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to a particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the camera 102 or a separate video system may capture video of the dentition from the point of view of the camera 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The object 104 may also, or instead, include a dental model, such as a plaster cast, a wax-up, an impression, or a negative impression of a tooth, teeth, soft tissue, or some combination of these.

The computer 108 may include, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may be further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the object 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display or the like capable of displaying stereo images.

Communications between the computer 108 and the camera 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the camera 102 to the computer 108 may be secured. The computer 108 may generate control signals to the camera 102 which, in addition to image acquisition commands, may include conventional camera controls such as focus or zoom.

In an example of general operation of a three-dimensional image capture system 100, the camera 102 may acquire two-dimensional image sets at a video rate while the camera 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system may employ camera motion estimation to avoid the need for independent tracking of the position of the camera 102. One useful example of such a technique is described in commonly-owned U.S. application Ser. No. 11/270,135, filed on Nov. 9, 2005, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In general, the display 110 may be operatively coupled to, and capable of receiving display signals from, the computer 108. This display may include a CRT or flat panel monitor, a three-dimensional display (such as an anaglyph display), an autostereoscopic three-dimensional display or any other suitable two-dimensional or three-dimensional rendering hardware. In some embodiments, the display may include a touch screen interface using, for example capacitive, resistive, or surface acoustic wave (also referred to as dispersive signal) touch screen technologies, or any other suitable technology for sensing physical interaction with the display 110.

The system 100 may include a computer-usable or computer-readable medium. The computer-usable medium 118 may include one or more memory chips (or other chips, such as a processor, that include memory), optical disks, magnetic disks or other magnetic media, and so forth. The computer-usable medium 118 may in various embodiments include removable memory (such as a USB device, tape drive, external hard drive, and so forth), remote storage (such as network attached storage), volatile or non-volatile computer memory, and so forth. The computer-usable medium 118 may contain computer-readable instructions for execution by the computer 108 to perform the various processes described herein. The computer-usable medium 118 may also, or instead, store data received from the camera 102, store a three-dimensional model of the object 104, store computer code for rendering and display, and so forth.

Figure 2:
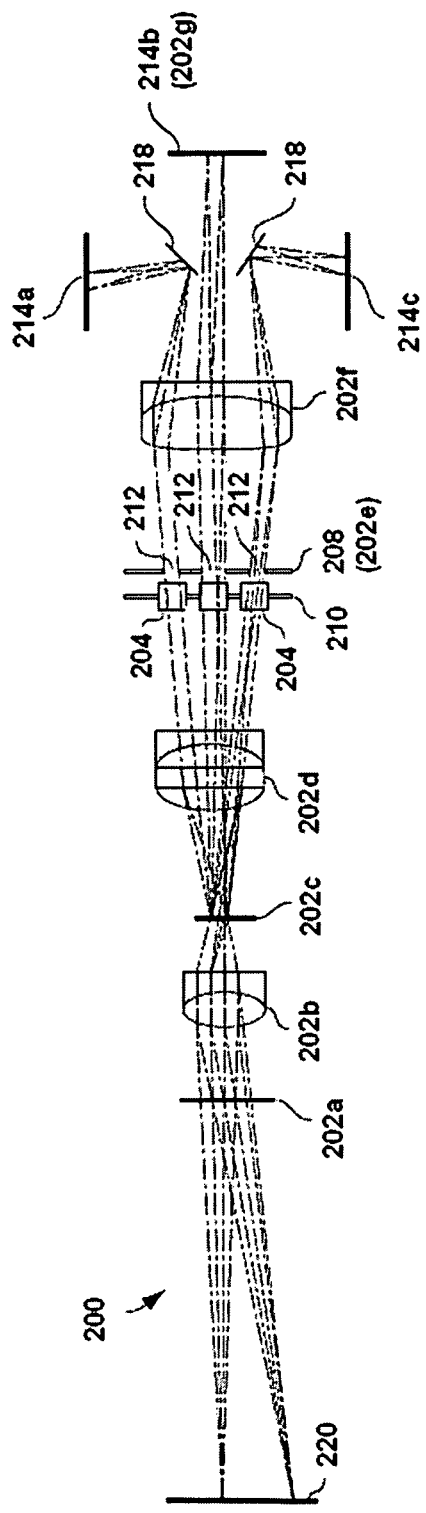
FIG. 2 shows a schematic diagram of an optical system for a three-dimensional camera.

FIG. 2 depicts an optical system 200 for a three-dimensional camera that may be used with the systems and methods described herein, such as for the camera 102 described above with reference to FIG. 1.

The optical system 200 may include a primary optical facility 202, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The optical system 200 may include a single primary lens, a group of lenses, an object lens, mirror systems (including traditional mirrors, digital mirror systems, digital light processors, or the like), confocal mirrors, and any other optical facilities suitable for use with the systems described herein. The optical system 200 may be used, for example in a stereoscopic or other multiple image camera system. Other optical facilities may include holographic optical elements or the like. In various configurations, the primary optical facility 202 may include one or more lenses, such as an object lens (or group of lenses) 202b, a field lens 202d, a relay lens 202f, and so forth. The object lens 202b may be located at or near an entrance pupil 202a of the optical system 200. The field lens 202d may be located at or near a first image plane 202c of the optical system 200. The relay lens 202f may relay bundles of light rays within the optical system 200. The optical system 200 may further include components such as aperture elements 208 with one or more apertures 212, a refocusing facility 210 with one or more refocusing elements 204, one or more sampling facilities 218, and/or a number of sensors 214a, 214b, 214c.

The optical system 200 may be designed for active wavefront sampling, which should be understood to encompass any technique used to sample a series or collection of optical data from an object 220 or objects, including optical data used to help detect two-dimensional or three-dimensional characteristics of the object 220, using optical data to detect motion, using optical data for velocimetry or object tracking, or the like. Further details of an optical system that may be employed as the optical system 200 of FIG. 2 are provided in U.S. Pat. No. 7,372,642, the entire content of which is incorporated herein by reference. More generally, it will be understood that, while FIG. 2 depicts one embodiment of an optical system 200, numerous variations are possible.

Figure 3:
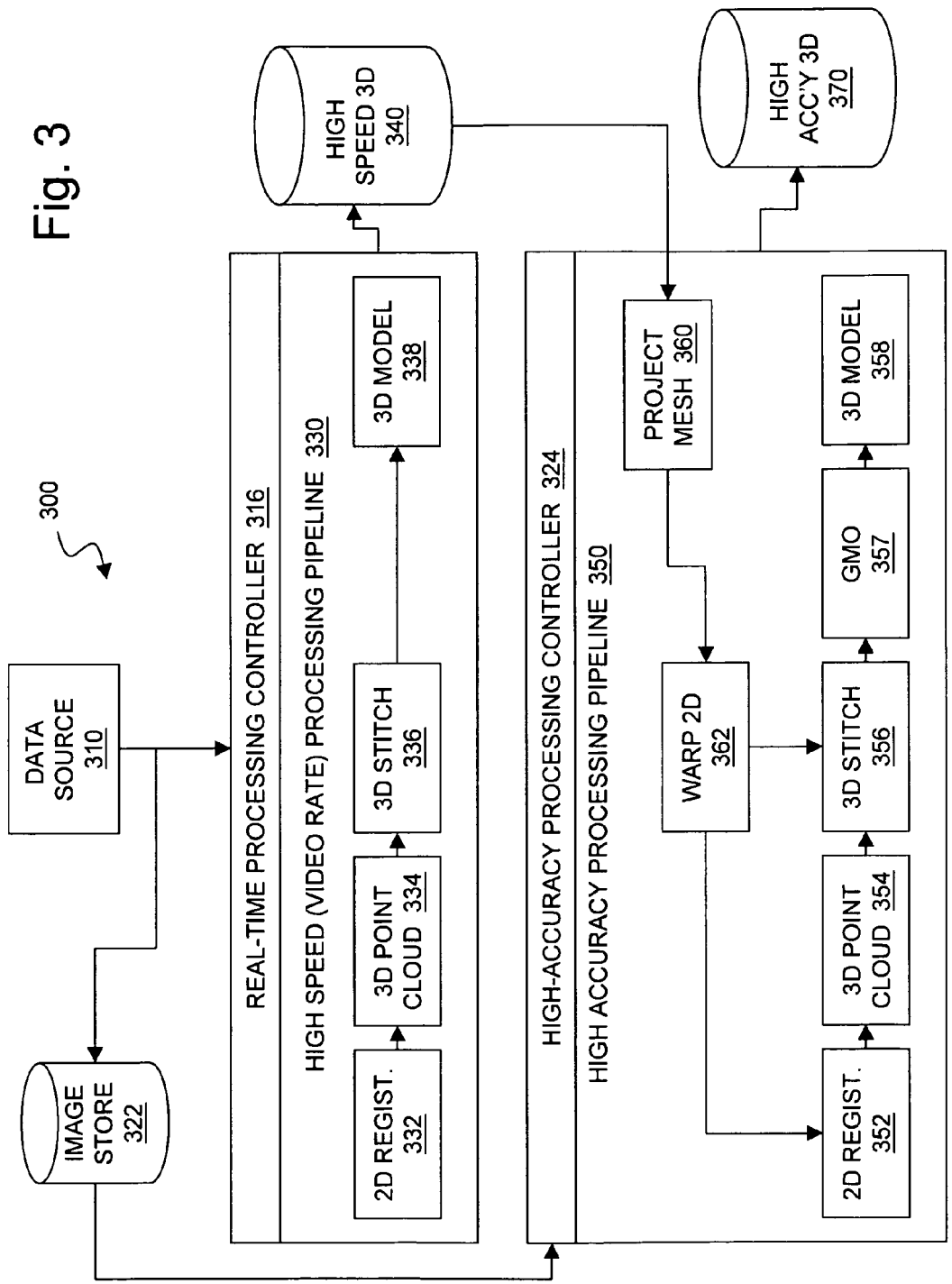
FIG. 3 shows a processing pipeline for obtaining three-dimensional data from a video camera.

FIG. 3 shows a three-dimensional reconstruction system 300 employing a high-speed pipeline and a high-accuracy pipeline. In general, the high-speed processing pipeline 330 aims to provide three-dimensional data in real time, such as at a video frame rate used by an associated display, while the high-accuracy processing pipeline 350 aims to provide the highest accuracy possible from camera measurements, subject to any external computation or time constraints imposed by system hardware or an intended use of the results. A data source 310 such as the camera 102 described above provides image data or the like to the system 300. The data source 310 may for example include hardware such as LED ring lights, wand sensors, a frame grabber, a computer, an operating system and any other suitable hardware and/or software for obtaining data used in a three-dimensional reconstruction. Images from the data source 310, such as center channel images containing conventional video images and side channels containing disparity data used to recover depth information may be passed to the real-time processing controller 316. The real-time processing controller 316 may also provide camera control information or other feedback to the data source 310 to be used in subsequent data acquisition or for specifying data already obtained in the data source 310 that is needed by the real-time processing controller 316. Full resolution images and related image data may be retained in a full resolution image store 322. The stored images may, for example, be provided to the high-accuracy processing controller 324 during processing, or be retained for image review by a human user during subsequent processing steps.

The real-time processing controller 316 may provide images or frames to the high-speed (video rate) processing pipeline 330 for reconstruction of three-dimensional surfaces from the two-dimensional source data in real time. In an exemplary embodiment, two-dimensional images from an image set such as side channel images, may be registered by a two-dimensional image registration module 332. Based on the results of the two-dimensional image registration, a three-dimensional point cloud generation module 334 may create a three-dimensional point cloud or other three-dimensional representation. The three-dimensional point clouds from individual image sets may be combined by a three-dimensional stitching module 336. Finally, the stitched measurements may be combined into an integrated three-dimensional model by a three-dimensional model creation module 338. The resulting model may be stored as a high-speed three-dimensional model 340.

The high-accuracy processing controller 324 may provide images or frames to the high-accuracy processing pipeline 350. Separate image sets may have two-dimensional image registration performed by a two-dimensional image registration module 352. Based on the results of the two-dimensional image registration a three-dimensional point cloud or other three-dimensional representation may be generated by a three-dimensional point cloud generation module 354. The three-dimensional point clouds from individual image sets may be connected using a three-dimensional stitching module 356. Global motion optimization, also referred to herein as global path optimization or global camera path optimization, may be performed by a global motion optimization module 357 in order to reduce errors in the resulting three-dimensional model 358. In general, the path of the camera as it obtains the image frames may be calculated as a part of the three-dimensional reconstruction process. In a post-processing refinement procedure, the calculation of camera path may be optimized—that is, the accumulation of errors along the length of the camera path may be minimized by supplemental frame-to-frame motion estimation with some or all of the global path information. Based on global information such as individual frames of data in the image store 322, the high-speed three-dimensional model 340, and intermediate results in the high-accuracy processing pipeline 350, the high-accuracy model 370 may be processed to reduce errors in the camera path and resulting artifacts in the reconstructed model. As a further refinement, a mesh may be projected onto the high-speed model by a mesh projection module 360. The resulting images may be warped or deformed by a warping module 362. Warped images may be utilized to ease alignment and stitching between images, such as by reducing the initial error in a motion estimate. The warped images may be provided to the two-dimensional image registration module 352. The feedback of the high-accuracy three-dimensional model 370 into the pipeline may be repeated until some metric is obtained, such as a stitching accuracy or a minimum error threshold.

Figure 4:
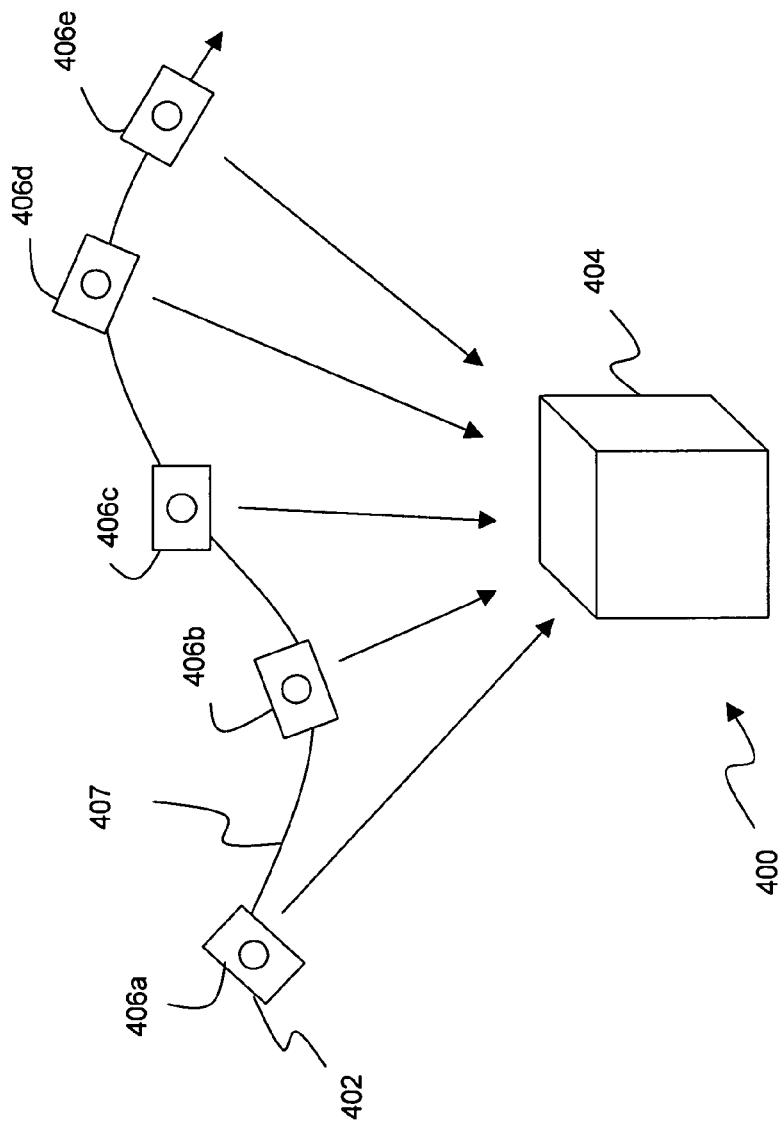
FIG. 4 illustrates a sequence of images captured from a moving camera.

FIG. 4 illustrates a coordinate system for three-dimensional measurements using a system such as the optical system 200 described above. The following description is intended to provide useful context, and should not be interpreted as limiting in any sense. In general an object 408 within an image plane 402 of a camera has world coordinates $\{X_w, Y_w, Z_w\}$ in a world coordinate system 410, camera coordinates $\{X_c, Y_c, Z_c\}$ in a camera coordinate system 406, and image set coordinates $\{x_i, y_i, d_i(x_i, y_i)\}$ for i=1 to N points or pixels within a processing mesh of the field of view 402, where $d_i$ is a disparity vector 412 containing one or more disparity values that characterize z-axis displacement ($Z_c$) or depth 404 of a point in the image plane 402 based upon x-axis and/or y-axis displacement in the image plane 402 between a number of physically offset apertures or other imaging channels. The processing mesh may be understood as any overlay or grid for an image or other two-dimensional data that identifies locations where processing will occur. While a processing mesh may be a regular grid of locations in a square, rectangular, triangular, or other pattern, the processing mesh may also, or instead, include irregular patterns selected randomly or according to the specific subject matter being processed. The disparity vector 412 may be expressed, for example, in terms of displacement relative to a center channel, if any, for the camera. In general, the disparity vector 412 encodes depth, and in various other three-dimensional imaging systems, this disparity vector 412 may be replaced by one or more other measured quantities that encode depth. Thus terms such as disparity vector, disparity value, and disparity data and the like should be understood broadly to include any one or more scalar and/or vector quantities measured by a system to capture depth information. Also more generally, a three-dimensional measurement as used herein may refer to any form of data encoding three-dimensional data including without limitation, groups of two dimensional images from which disparity vectors might be obtained, the disparity field (of disparity vectors) itself, or a three-dimensional surface reconstruction derived from the disparity field. In image-based three-dimensional reconstruction, a camera model may be employed to relate disparity vectors to depth within a field of view of a camera. The camera model may be determined theoretically based upon optical modeling or other physics, empirically through observation, or some combination of these, and may be calibrated to compensate for optical aberrations, lens defects, and any other physical variations or features of a particular physical system.

While a single image plane 402 is illustrated for purposes of explanation, it will be appreciated that a multi-aperture camera (or other multi-channel system) may have a number of physically offset optical channels that provide a different image plane for each channel, and the differences in feature locations (the x-y displacement) between the images for each optical channel may be represented as the disparity field. In various certain processing steps, the disparity data may be referenced to a single image plane such as a center channel image plane of the camera.

Figure 5:
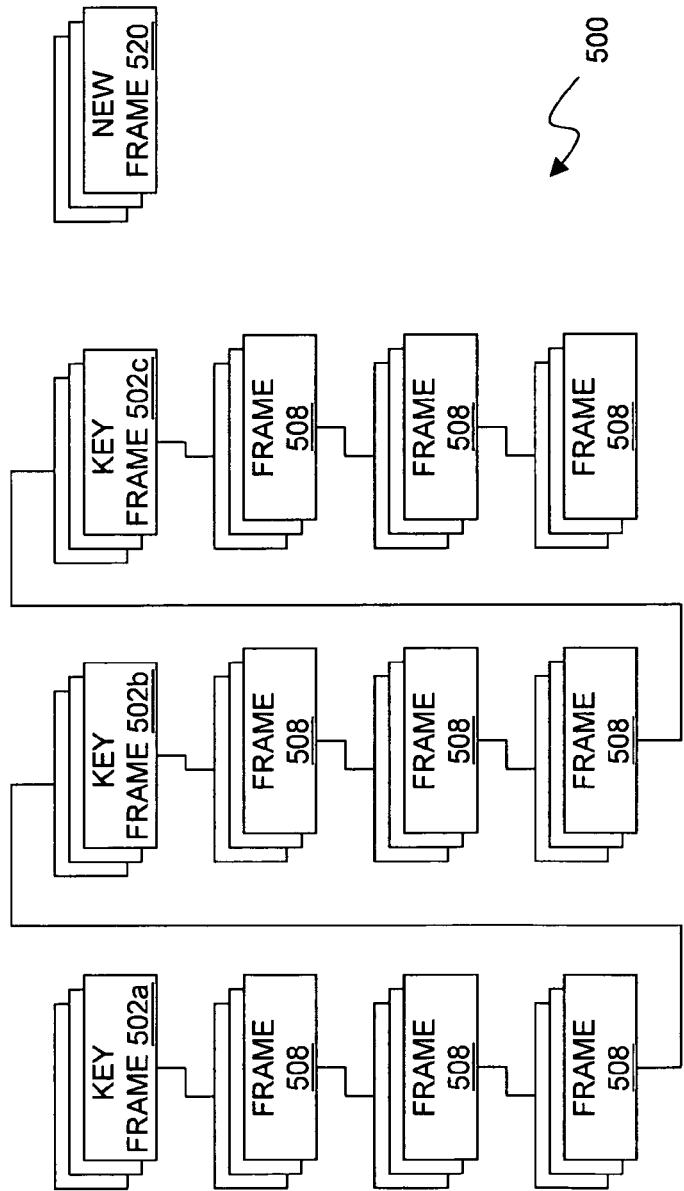
FIG. 5 illustrates a series of frames of image data.

FIG. 5 illustrates a series of frames of image data. As described above, each one of the frames 500 of image data may include image sets including, e.g., two-dimensional images from a center channel and one or more side channels of a three-dimensional camera. In one embodiment, the side channels may contain disparities relative to each other or the center channel that encode depth information used to recover points in three dimensions, although the methods and systems described herein may be usefully adapted to various other techniques for capturing frames of three-dimensional information for a motion-based three-dimensional reconstruction. The frames 500 may include a number of key frames 502 and a number of other, non-key frames 508. A variety of techniques are possible for selecting key frames, and storing various types of more complete data with key frames 502 than other frames 508. In one aspect, the key frames 502 may be selected to contain sufficient overlapping data to reconstruct a camera path using only key frames. The key frames 502 may also or instead be selected based upon sequential frame separation, physical proximity, or any other useful metric for creating a subset of the full sequence of frames 500 for enhanced processing. Processing constraints or design preferences may also influence key frame selection. For example, the total number of key frames may be limited, or the number of frames between key frames may be limited. As another example, a certain minimum or maximum amount of motion (or both) between camera positions (and/or orientation) may be desired for key frames. In one aspect, image sets for frames 508 between the key frames may be discarded, retaining only the three-dimensional data and camera translation/rotation for each non-key frame 508. At the same time, more complete data may be retained for key frames 502, such as full resolution image sets, sequence numbers, links to other key frames 502, image signature data described below (e.g., compressed images, image signatures with rotational and translational offsets, etc.), and so forth. During a three-dimensional scan, a camera path may be created with each frame 500 sharing overlapping subject matter with each previous frame and each subsequent frame. However, when this scan is paused, either intentionally by a user or due to reconstruction errors (i.e., an object moving outside a scan volume for a camera, excess displacement causing an inability to connect a new frame to a previous frame, or any other events causing a loss of image data or camera path), a process may be initiated to reattach a new frame 520 for a current view of the camera to any other frame 500 stored by the system. Techniques for creating image signatures to use in this process are described with reference to FIGS. 6-9. A process for using these image signatures is described with reference to FIG. 10.

In one aspect, images used for a signature such as the image 500 in FIG. 5 may be adjusted to a substantially common scale or centroid distance in order to normalize magnification for purposes of matching. This may be accomplished, for example, by determining a centroid for a three-dimensional reconstruction recovered from a frame of data, and estimating or calculating a depth or distance from the camera position for this single point. By scaling various target images (key frames and/or other frames) and/or a search image (e.g., the current camera view), to a common depth, the effects of magnification can be mitigated.

Figure 6:
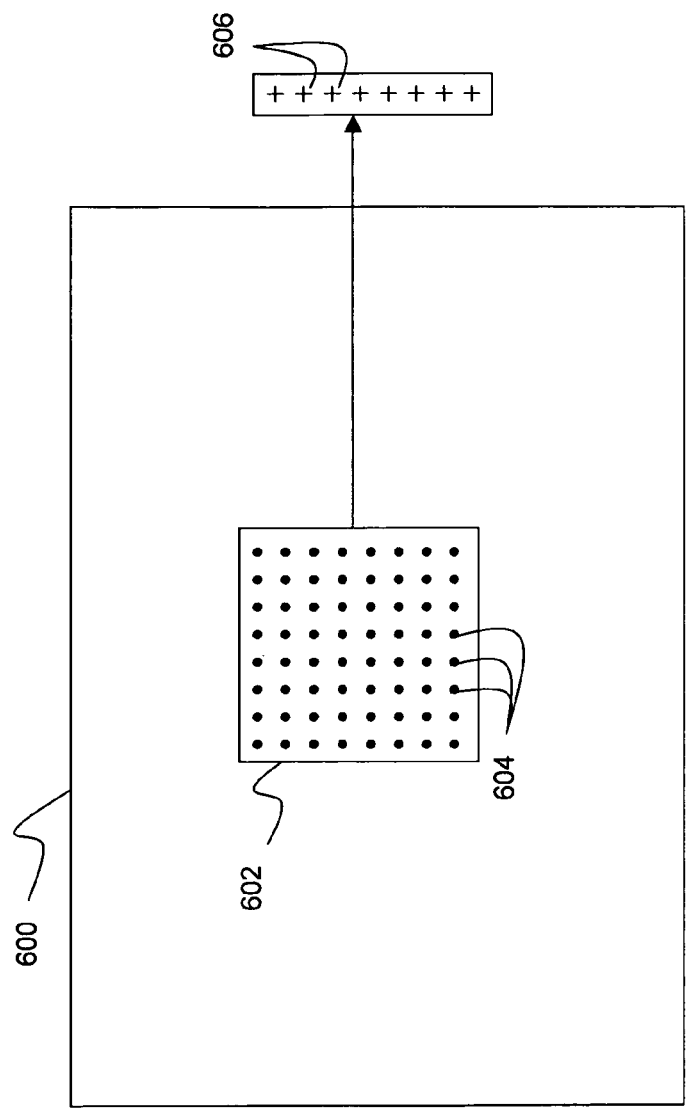
FIG. 6 shows an image signature for a two-dimensional image.

FIG. 6 shows an image signature for a two-dimensional image. An image 600, which may be for example an image from any of the frames of image data described above, may contain a number of pixels that encode two-dimensional image data. The image 600 may, for example, be a full resolution image or a compressed image such as a half-resolution image, a quarter-resolution image, or any image of any other useful dimensions. It will be appreciated that the techniques described herein may usefully be employed on downsampled or lower-resolution images in order to conserve processing resources. For example, a full resolution 1024×768 pixel image may be converted to a 64×48 pixel image for use as the image 600 upon which image signature calculations are performed. In order to obtain an image signature, a center region 602 of the image 600 may be identified that contains a number of pixels 604. It will be understood that, while a specific number of pixels is depicted in FIG. 6, this number of pixels is shown for purposes of illustration and does not limit the scope of the invention. Any useful number of pixels may be used, including square arrays such as eight-by-eight, sixteen-by-sixteen, thirty two-by-thirty two, or any other useful square, rectangular, or other shaped and sized window of pixels from the image 600. Each row of pixel values in the center region may be averaged to provide a row average 606 for that row, and the row averages 606 may be stored in a linear array 608 that represents a signature for the image 600.

In one embodiment, this image signature is calculated for each current image when trying to reattach to a sequence of frames after pausing, as further described below.

Figure 7:
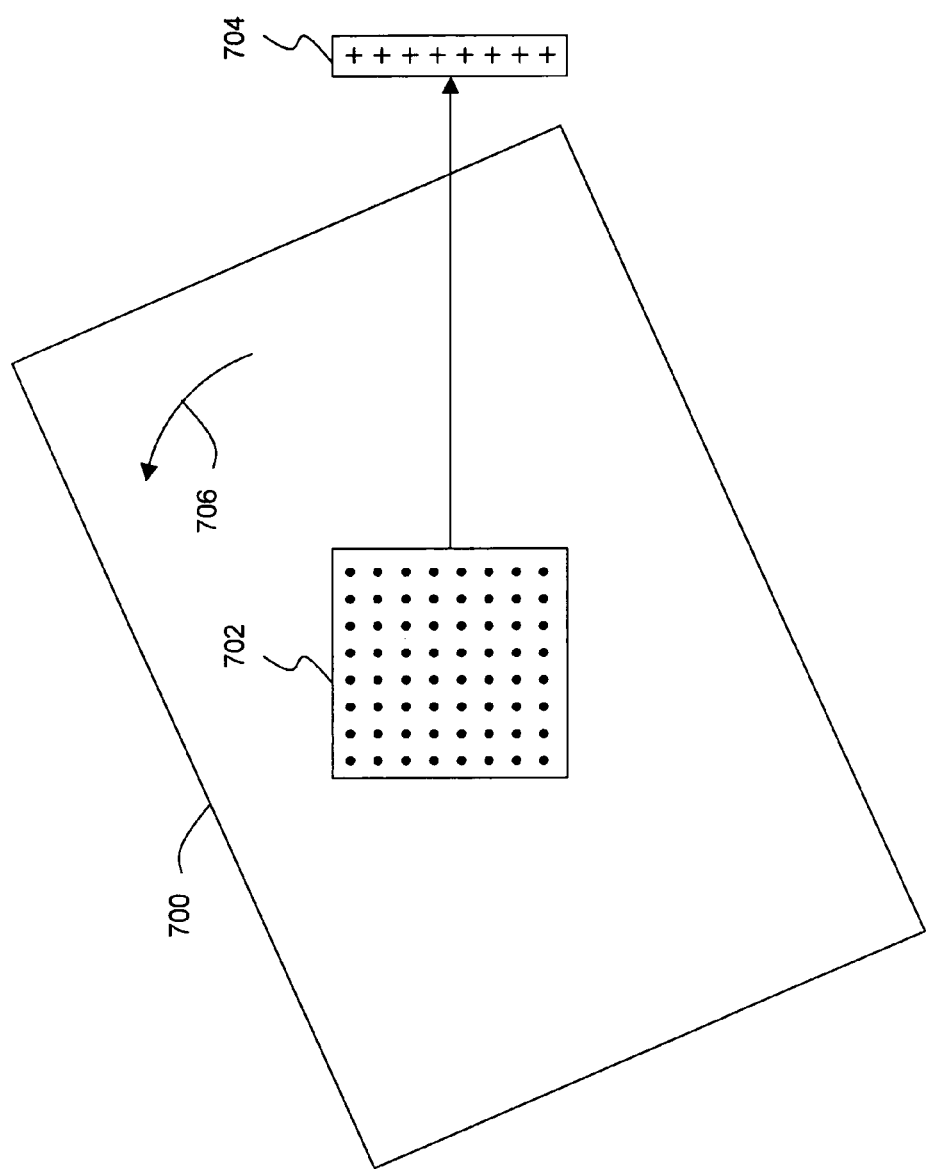
FIG. 7 shows an image signature with a rotational offset.

FIG. 7 shows an image signature with a rotational offset. The image 700 may be rotated (or the center region 702 may be rotated) and rows of pixel values in the center region 702 may be averaged to provide a row average, and the row averages for the center region 702 may be stored in a linear array 704 that represents an image signature with an offset rotation 706. Any number of rotationally offset signatures may be generated. For example, the image 700 may be rotated in steps of, e.g., ten degrees through an entire circle, or through a portion of a circle such as −40 degrees to +40 degrees around the original orientation (resulting in nine rotationally offset image signatures). It will be understood that rotation as referred to herein refers to relative rotation of the image 700 relative to the center region 702. As an analytical matter, it should not matter whether the image 700 is rotated or the center region 702 is rotated, although there may be computational efficiency to one of these options. For example, if the center region 702 is rotated, there may a smaller number of calculations required to determine values within the rotated window of the center region 702. As used in this context, rotation is specifically intended to refer to the relative rotation of these images without reference to which of the two images is rotated into the coordinate system of the other. In embodiments of the hand-held camera described above, rotational increments may be centered around expected manual orientations during a scan.

Figure 8:
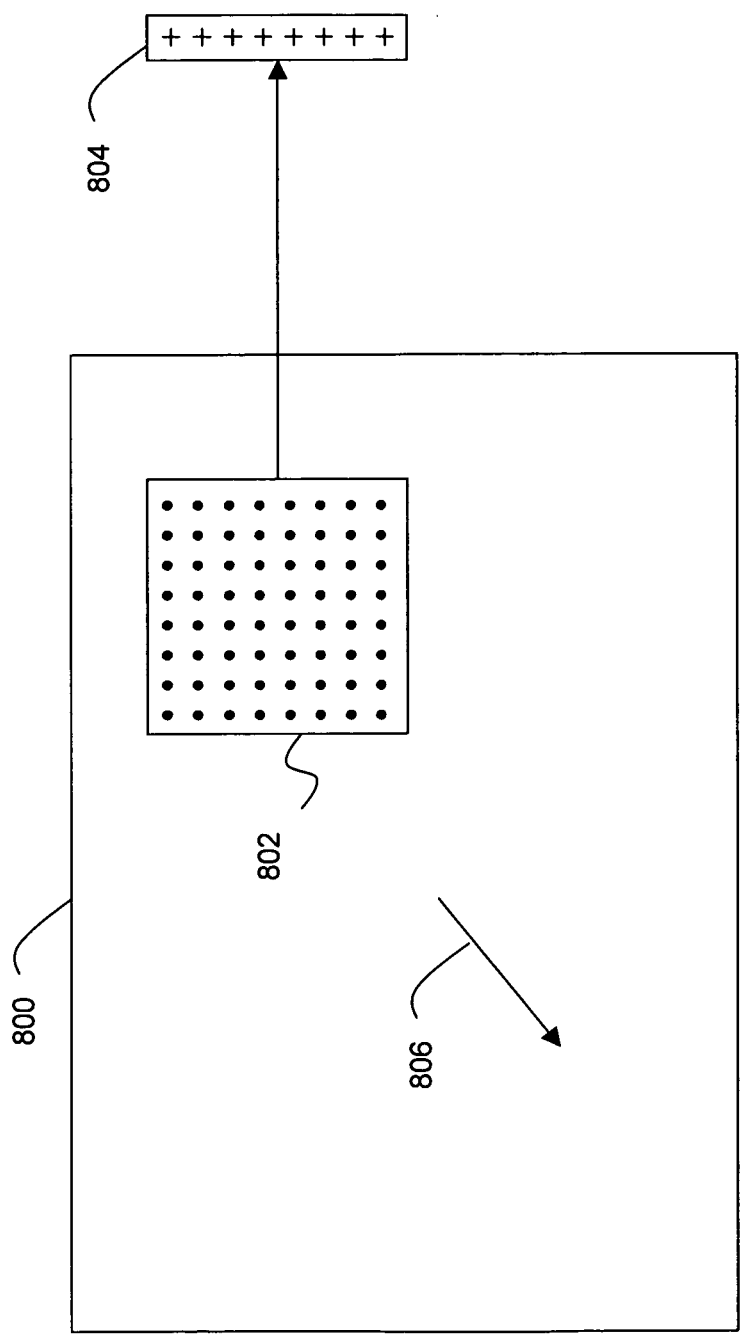
FIG. 8 shows an image signature with a translational offset.

FIG. 8 shows an image signature with a translational offset. The image 800 may be translated (or the center region 802 may be translated) and rows of pixel values in the center region 802 may be averaged to provide a row average, and the row averages for the center region 802 may be stored in a linear array 804 that represents an image signature with an offset translation 806. Any number of translationally offset signatures may be generated. For example, the image 800 may be translated in steps of, e.g., one pixel in the x and y axis, or along a single axis (with rotation potentially capturing translation information along the orthogonal axis). It will be understood that translation as referred to herein refers to relative translation of the image 800 relative to the center region 802. As an analytical matter, it should not matter whether the image 800 is translated or the center region 802 is translated, although there may be computational efficiency to one of these options. For example, if the center region 802 is translated, there may a smaller number of calculations required to determine values within the translated window of the center region 802. As used in this context, translation is specifically intended to refer to the relative translation of these images without reference to which of the two images is translated into the coordinate system of the other.

In one embodiment, nine rotations may be employed, with nine translations for each rotation yielding eighty one image signatures covering various orientations of an image for each key frame of data. Where rotations and translations are centered around the original image orientation, one of the image signatures may capture a zero rotation, zero translation signature for the original orientation. In order to improve processing speed when searching for a current image in the catalogue of image data, these multiple image signatures may be averaged on an element-by-element basis to provide a single linear array representing the average signature for an image. It will be understood that, while certain motion-based systems contain multiple two-dimensional images for each frame of data, a single image from each image set, such as the conventional still image from a center channel or similar camera, may be usefully employed to improve consistency between a signatures for a search image and the target images in the catalogue of frames 500 described above.

Figure 9:
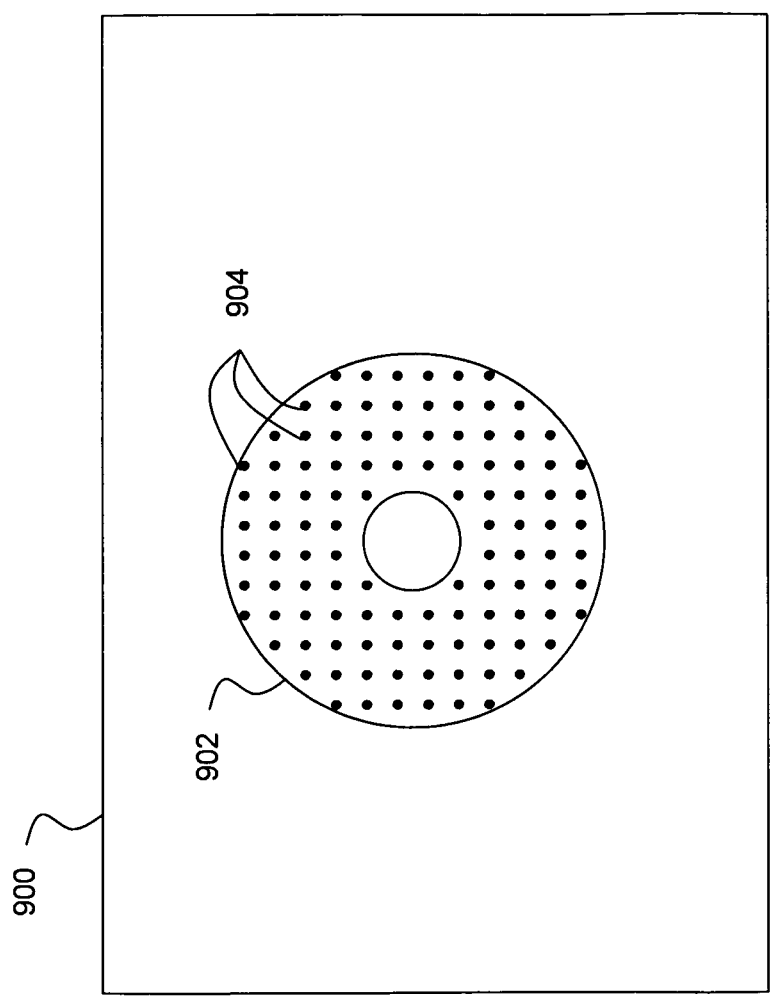
FIG. 9 shows a window for a spatial frequency signature.

FIG. 9 shows a window for a spatial frequency signature. In addition to rotations and translations of an image as described above, a spatial frequency signature may be obtained for an image 900 using a window 902 to select pixels 904 in the image 900 and performing a two-dimensional transform such as a Fast Fourier Transform ("FFT") to place the windowed pixel values into a spatial frequency domain representation. As described below in more detail, this spatial frequency signature may be used in combination with the spatial signatures described above to improve a search for images matching a current view in the catalogue of frames 500 of data for an existing scan.

Figure 10:
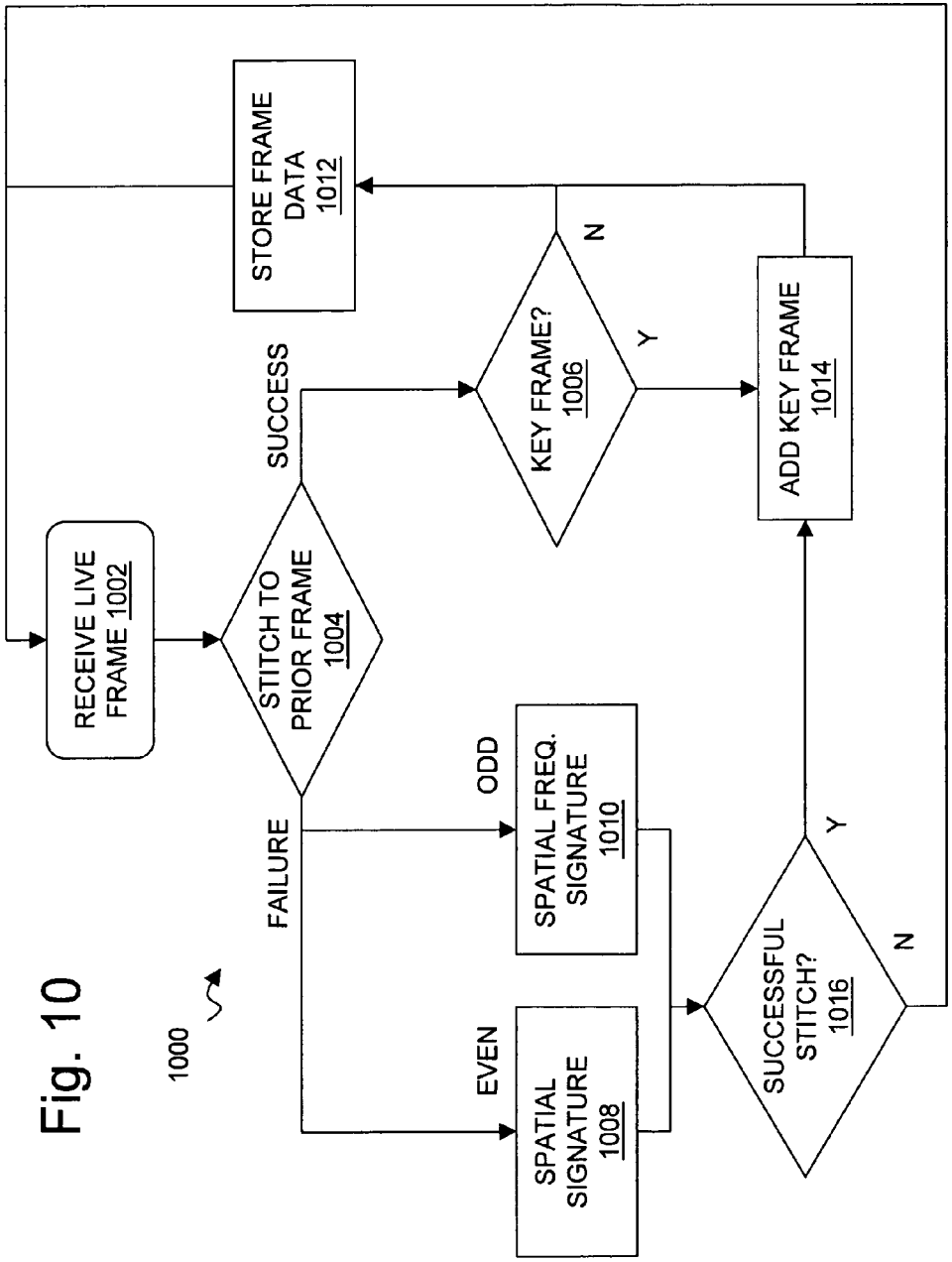
FIG. 10 shows a process for using image signatures to reattach to an existing three-dimensional scan.

FIG. 10 shows a process for using image signatures to reattach to an existing three-dimensional scan. The process 1000 may begin with receiving a live frame as shown in step 1002. This live frame (also referred to herein as the current view) represents a current frame of image data from a three-dimensional camera, such as any of the cameras described above, from a current position (and orientation) of the camera. In one embodiment, the live frame may include an image set with a center channel image that contains a conventional two-dimensional image of scanned subject matter, along with two side channel images from offset optical axes.

As shown in step 1004 the live frame may be stitched to a prior frame (which may be a key frame or a non-key frame) in order to recover a camera translation and rotation for the live frame and add recovered three-dimensional data to a three-dimensional model. If the stitch is successful, e.g., such that the three-dimensional data from successive frames of data register to one another with sufficient accuracy, the process 1000 may proceed to step 1006. If the stitch is unsuccessful, the process 1000 may optionally proceed to step 1008 or 1010 as generally discussed below.

As shown in step 1006, once a current or live frame has been stitched to the existing catalogue of frames of data, a determination may be made whether the frame is a key frame. This may be based on any of the criteria discussed above, such as relative overlap with other key frames, sequential separation from a previous key frame, spatial separation (in recovered camera position) from other key frames, and so forth.

If the frame is not a key frame, the process 1000 may proceed to step 1012 where the non-key frame is stored. This may include, for example storing recovered data such as a camera position, orientation, and a three-dimensional point cloud or the like, and discarding source data such as the full resolution image set for the frame. In an embodiment, the full resolution image set may be temporarily retained for each frame after the most recent key frame, or for an immediately proceeding non-key frame. In such an embodiment, when a new key frame is created, the non-key frames between the new key frame and the previous key frame may be deleted in whole or in part.

If the frame evaluated in step 1006 is selected as a key frame, the frame may be added to the catalogue of scan data as a key frame. In addition to retaining the full resolution data for the key frame (in step 1012), additional processing may be performed on key frames. For example, any of the signatures described above may be calculated for each key frame. In one embodiment, this includes a number of linear arrays for a number of rotational and translational offsets as generally described above. This may also include an average of these linear arrays for use in signature-based searches for matching frame content.

In one embodiment, a key frame image (or a reduced version of a key frame image) may be processed to obtain an average for each one of a plurality of rows of pixels in a center region of the image to provide a linear array of row averages stored as a first signature. The center region may then be rotated and translated relative to the image over any number of permutations, with a linear array of rotated and/or translated row averages calculated for each. The resulting arrays may be stored as image signatures for the key frame. In addition, an element-by-element average of these arrays may be calculated and stored as a summary image signature for the image. After the key frame has been processed, the process 1000 may proceed to 1012 where key frame data is stored, and the process 1000 may return to step 1002 where a next live frame of data is obtained from a camera.

Returning to step 1002, if a stitch fails for any reason (either through camera or operator error, or by specific user instruction), the process 1000 may optionally proceed to step 1008 where a spatial signature is used for image matching, or step 1010 where a spatial frequency signature is used for image matching. These approaches may be alternately employed according to, e.g., whether the live frame has an even or odd sequential frame number, or using any other suitable weighted or unweighted technique.

As shown in step 1008, a spatial signature may be employed to compare two-dimensional data from the live frame to key frames or other frames stored in the frame catalogue. In one embodiment, a spatial signature is calculated for the live frame using the technique described above with reference to FIG. 6. Although any translation or rotation may be employed for this signature, the signature may advantageously operate on a centered, unrotated window for a compressed version of the center channel image from the live frame.

A variety of techniques may be employed to use the spatial signature information for image matching. One approach may operate as follows in order to refine the search area over a number of steps before a full three-dimensional registration of recovered three-dimensional data is attempted. The live frame signature may be compared to key frames in the catalogue of frames based upon the summary signature (a single, linear array of the element-by-element average of signatures from various orientations for the frame, as described above) calculated for each of the key frames. This comparison may be calculated for example as the normalized cross-correlation of the summary signature and the live frame signature, or using any other suitable measure of similarity. This relatively computationally simple comparison may, for example, be performed for all key frames in the catalogue for a scan or all of the key frames for a specific area of interest in the reconstructed three-dimensional model. The resulting key frame comparisons based on the summary signature may be ranked or scored using any suitable approach to identify a number of candidate images, such as the best n candidate images on a quantitative basis, or all key frames having a matching score above a predetermined threshold.

For each of the candidate images, a comparison may be made between the image signature for the live frame and each rotated and translated signature for each (key frame) candidate image. In an example embodiment using eighty-one signatures for each key frame, eighty-one comparisons may be made for each of the candidate images. The resulting comparisons may be ranked or scored, again using any suitable similarity measure, to identify key frames that are good candidates for registration. This may be an absolute number (e.g., the key frames with the top five individual results, or the top five key frames based upon individual results), or a variable number based on a predetermined threshold.

As shown in step 1016, these registration candidates—e.g., the key frames containing the five (or less or more) best individual matches to the live image signature—may be test-registered to the live frame in a full stitching operation such as that described above in step 1004. A quality score may be evaluated for each stitch based on, e.g., the error in the stitch or any other residual or cost function for the stitch. In one embodiment, the first stitch to a key frame meeting some predetermined threshold quality criterion may be selected as a next key frame for the catalogue. In another embodiment, a stitch to each key frame may be fully resolved, and the best stitch may be selected based on a quality score. If at least one stitch to a registration candidate succeeds, the live frame may be added to the catalogue as a key frame as shown in step 1014. If no stitch to a registration candidate succeeds, the process 1000 may return to step 1002 where a new live frame is captured.

As shown in step 1010, a spatial frequency signature may be employed instead of (or in certain embodiments, in addition to) a spatial signature to compare a live frame to other frames of data. In general, this may include a frequency domain comparison of the live frame to other frames, using, e.g., a windowed FFT of a compressed image, or any other suitable frequency domain representation. In one embodiment, the spatial frequency signature may be compared to one or more recent non-key frames after the last key frame. In another embodiment, the spatial frequency signature may be compared exclusively to the single most recent frame of data successfully stitched to the existing three-dimensional model. It will be understood that in this context, a comparison may include estimating rotation and translation based upon spatial frequency spectra, and attempting a stitch based on these parameters. It will be appreciated that rotation information from the spatial frequency signature of a live frame and a registration candidate may also be used in other circumstances, such as when attempting to resume a scan with a substantially rotationally re-oriented scanner. This motion is expected, for example, when a handheld camera such as that described in reference to FIG. 1, is switched from one hand of a user to the other hand and a user is attempting to reattach to a scan at the same physical location where the scan was paused. In such circumstances, the spatial frequency signature may usefully be applied to a recent history of key frames where suitably matching camera positions might be found.

In one embodiment, the process 1000 may alternate on a regular basis (such as odd and even frames) between a comparison using a spatial signature (step 1008) and a comparison using a spatial frequency signature (step 1010). In this alternating comparison, the frames processed using a spatial signature may be unique from the frames processed using a spatial frequency signature, such as by using a spatial signature for all key frames in one iteration, and using a spatial frequency signature for one or more sequentially recent non-key frames in a next iteration. More generally, it should be understood that numerous other protocols may be suitably employed to alternate between these two approaches to achieve the combined advantages of each matching technique while reducing computational burden. In other embodiments, both techniques may be employed concurrently for each new live frame of data, or the process 1000 may use some combination of these approaches. As shown in step 1016, the results of a test registration, if successful may be added as a key frame 1014 to the scan catalogue. If the test registration is not attempted, or is unsuccessful, then the process 1000 may return to step 1002 where a next live frame is received from the camera.

It will be appreciated that any of the above system and/or methods may be realized in hardware, software, or any combination of these suitable for the data acquisition and modeling technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. Thus in one aspect there is disclosed herein a computer program product comprising computer executable code that, when executing on one or more computing devices, performs any and/or all of the steps described above. At the same time, processing may be distributed across devices such as a camera and/or computer and/or fabrication facility and/or dental laboratory and/or server in a number of ways or all of the functionality may be integrated into a dedicated, standalone device. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method for creating a signature for image matching comprising:

providing an image containing a plurality of pixels;

creating an average for each one of a plurality of rows of pixels in a region of the image to provide a linear array of row averages stored as a first signature, wherein the region includes a predetermined arrangement of pixels within the image;

rotating the region relative to the image to provide a rotated image;

creating an average for each one of a plurality of rows of pixels in the rotated image to provide a linear array of rotated row averages stored as a second signature;

translating the region relative to the image to provide a translated image;

creating an average for each one of a plurality of rows of pixels in the translated image to provide a linear array of translated row averages stored as a third signature; and determining an element-by-element row average for each signature of the image including at least the first signature, the second signature, and the third signature, and storing the element-by-element row average as a summary image signature descriptive of the image.

2. The method of claim 1 wherein the image is a compressed version of a source image having a greater number of pixels.

3. The method of claim 1 further comprising translating the region into a plurality of offset positions relative to the image and obtaining another linear array of row averages from the region for each one of the plurality of offset positions.

4. The method of claim 3 further comprising rotating the region, after it has been translated to each one of the plurality of offset positions, into a plurality of offset orientations relative to the image and obtaining another linear array of row averages from the region for each one of the combined offset positions and offset orientations.

5. The method of claim 3 wherein the plurality of translations include offsets of one pixel along an x axis and a y axis.

6. The method of claim 3 wherein the plurality of translations include offsets of one pixel along a single axis.

7. The method of claim 1 further comprising rotating the region into a plurality of offset orientations relative to the image and obtaining another linear array of row averages from the region for each one of the plurality of offset orientations.

8. The method of claim 7 wherein the plurality of offset rotations include a plurality of equally offset rotations.

9. The method of claim 8 wherein the plurality of offset rotations includes offsets in increments of ten degrees.

10. The method of claim 8 wherein the plurality of offset rotations rotate the image through an entire circle.

11. The method of claim 1 further comprising:
receiving a second image;
creating an average for each one of a plurality of rows of pixels in a second region of the second image to provide a linear array of row averages stored as a search signature; and
comparing the summary image signature to the search signature to identify a potential match.

12. The method of claim 11 wherein the second image is a live frame of image data from a three-dimensional camera.

13. The method of claim 1 wherein the region includes an eight-by-eight array of pixels.

14. The method of claim 1 wherein the region includes a sixteen-by-sixteen array of pixels.

15. The method of claim 1 wherein the region includes a thirty two-by-thirty two array of pixels.

16. The method of claim 1 wherein the region includes a square window of pixels from the image.

17. The method of claim 1 wherein the region includes a rectangular window of pixels from the image.

18. The method of claim 1 further comprising performing a two-dimensional transform on a window of pixel values within the image, thereby providing a spatial frequency signature for the image.

19. The method of claim 18 wherein the two-dimensional transform is a Fast Fourier Transform.

20. The method of claim 18 further comprising alternately attempting matches to a catalogue of image data using the spatial frequency signature and the summary image signature.

* * * * *